United States Patent [19]

Shell et al.

[11] Patent Number: 4,865,850

[45] Date of Patent: Sep. 12, 1989

[54] DIETARY FAT REDUCTION

[75] Inventors: William E. Shell, Los Angeles; Jackie R. See, Fullerton, both of Calif.

[73] Assignee: See/Shell Biotechnology, Inc., La Mirada, Calif.

[21] Appl. No.: 904,410

[22] Filed: Sep. 8, 1986

[51] Int. Cl.⁴ .................. A61K 9/18; A61K 9/42; B01J 13/02

[52] U.S. Cl. .................. 424/491; 424/456; 424/476; 424/498; 428/402.24; 514/909; 514/951

[58] Field of Search .......... 428/402.24; 424/476, 424/491, 498; 514/909, 957

[56] References Cited

U.S. PATENT DOCUMENTS

| | | | |
|---|---|---|---|
| 3,649,347 | 3/1972 | Battista | 424/491 X |
| 4,407,795 | 10/1983 | Nicolau et al. | 514/58 |
| 4,447,412 | 5/1984 | Bilton | 424/498 |
| 4,533,542 | 8/1985 | Buddenbaum et al. | 424/498 X |
| 4,590,170 | 5/1986 | Akiyoshi et al. | 436/533 |
| 4,597,762 | 7/1986 | Walter et al. | 435/69 X |
| 4,602,005 | 7/1986 | Malinow | 514/26 |
| 4,747,881 | 5/1988 | Shaw et al. | 424/476 X |

Primary Examiner—Richard D. Lovering
Attorney, Agent, or Firm—Robert J. Schaap

[57] ABSTRACT

A method and a composition for accumulating and the binding of food fats in an animal body gastrointestinal tract. The method and composition rely upon non-biodegradable collagen particles, such as microspheres, having a size of at least two microns and a fat receptor, such as bile, capable of having food fat adhered thereto on the surface of the particles. These particles are sufficiently large so that they do not pass through the surface mucosa of the gastrointestinal tract and permit the particles with the food fat to pass through the gastrointestinal tract and out of the body through animal excretion.

2 Claims, 1 Drawing Sheet

DIETARY FAT REDUCTION

BACKGROUND OF THE INVENTION

1. Field of the Invention

This invention relates in general to certain new and useful improvements in dietary fat reduction, and more particularly, to a method and composition for accumulating and binding of food fats in an animal body gastrointestinal tract and permitting the food fats to pass through the tract and out of the body through body excretia.

2. Brief Description of the Prior Art

Weight reduction has been a significant problem, particularly in the industrialized and more affluent countries of the world, where food shortages are not pronounced. It has been well established that excess weight is not only undesirable from an aesthetic standpoint, but excess weight can result in or contribute to various health problems, and particularly coronary and coronary related problems.

There have been many proposed techniques and compositions to effectuate a weight reduction. Unfortunately, many of the currently available techniques and compositions can present serious adverse side effects if not properly used and thus, often require medical intervention and control. Notwithstanding, abuses with the currently available techniques and compositions can still occur.

Many of the presently available techniques and compositions to reduce weight rely upon controls over caloric in-take. However, the controls over caloric in-take are those which are most widely abused and which lead to serious adverse consequences including, but not limited to cases of drug dependence, such as amphetamine dependence.

Other compositions have been proposed to reduce gastric emptying. One known composition which has been studied as a control over gastric emptying and hence the amount of food in-take is guar gum. Still other fiber compositions have also been proposed to reduce gastric emptying time. While there are not necessarily serious side effects associated with some of the fiber compositions used to control gastric emptying achievement of weight reduction is relatively slow. As a result, the fiber compositions must be used over a substantial period of time. Many people become frustrated with only small incremental gains, i.e. weight decrease, and thus resort to more drastic remedies which can seriously affect their health. Accordingly, these gastric emptying compositions have met with only mild success.

Excess dietary fat in-take and absorption by the blood stream is one of the leading contributors to excess weight and therefore, it would be desirable to control dietary fat in-take. Various diets have been proposed for this purpose and which would be moderately effective in reducing fat-intake. However, essentially all of these diets compromise the culinary pleasures associated with food in-take and are oftentimes combinations of rather bland foods. Accordingly, many dieters abandon their dietary programs and hence their control over fat in-take.

It is also known that the in-take of dietary fats can result in increased levels of blood fats as for example, cholesterol and triglycerides. The increase of certain blood fats has also been established to be associated with increased risk of coronary problems. Hence, it is also desirable to reduce fat in-take in order to reduce the level of blood fats.

A cholestyramine resin offered under the trademark "Questran" has been available for reducing the cholesterol fat level in the blood stream. It has been found that there is an increased fecal loss of bile acids due to the administration of the cholestyramine powder resin. This leads to an increased oxidation of cholesterol to bile acids as well as a decreased beta lipoprotein and hence a decrease in serum cholesterol levels. However, many disadvantageous side effects have been associated with the administration of the Questeran cholestyramine resin powder. First of all, it has been found that the cholestyramine resin has a significant effect in delaying the absorption of other oral medicines. More importantly, there has been clear evidence that the administration of the cholestyramine resin prevents absorption of fat soluble vitamins. As a result, any fat soluble vitamins cannot be administered during the use of the cholestyramine resin. There has also been found to be a greater incidence of tumors occurring in rats when cholestyramine has been administered. Among the other side effects noted are adverse reactions during pregnancy, constipation, and abdominal discomfort. As a result, there is also some serious contra-indication for the use of cholestyramine in reducing serum cholesterol levels.

Heretofore, there has not been any demonstrably effective technique or composition for reducing the dietary fat absorption by the body without restrictive dietary plans. What is needed therefore is a composition and/or process which is capable of reducing the dietary fat metabolism and retention by the body without dietary controls.

OBJECTS OF THE INVENTION

It is, therefore, one of the primary objects of the present invention to provide a process and a composition which are capable of reducing dietary fat absorption by the body without restrictive dietary plans.

It is another object of the present invention to provide a process and a composition of the type stated which are highly effective in reducing dietary fat absorption by the body and which does not present any harmful side effects.

It is a further object of the present invention to provide a composition and a process of the type stated in which normal body functions are not materially affected.

It is an additional object of the present invention to provide a composition and a process of the type stated which controls fat-intake and retention and thereby leads to improved health.

It is also an object of the present invention to increase water absorption in the lower intestinal tract and thereby reduce constipation.

It is still another object of the present invention to provide a method and a composition for reducing the generation of low density lipoprotein, cholesterol and enabling the generation of a greater percentage of high density lipoprotein cholesterol by the body.

It is another salient object of the present invention to provide a method and composition of the type stated in which the emulsion of fat and the non-biodegradable particles are maintained in a liquid phase in the gastrointestinal tract.

With the above and other objects in view, my invention resides in the novel features and steps of the process and components of the composition and the uses thereof in combination.

BRIEF SUMMARY OF THE DISCLOSURE

In a broad aspect, the present invention relates to a method for accumulating and binding food fats in an animal body gastrointestinal tract to reduce absorption by the bloodstream of the animal body. The term "animal" and "animal body" is used in a broad sense to include all forms of animals, and particularly domesticated animals. However, the present invention is primarily useful with human beings.

The method comprises the introducing of non-biodegradable particles having fat receptors on the surfaces thereof into the gastrointestinal tract of an animal. The fat which is released from the food in an animal stomach will become attached to the fat receptors on the particles. This usually occurs below the stomach, as for example, in the duodenum. The fat attached particles are then allowed to pass through the gastrointestinal tract and out of the body through body excretia, such as the body stool.

In one important aspect of the present invention, the particles must have a size which are sufficiently large so that they will not pass through the surface mucosa of the gastrointestinal tract. Generally, the particles should have a size in the range of at least about two microns and more preferably from at least about five microns.

The particles which may be used may adopt the form of non-biodegradable fibers, or fibers, or other substances which are non-degradable. Collagen, for example, serves as an excellent particle in accordance with the present invention. The collagen is rendered non-biodegradable by cross-linking with a suitable reducing agent such as glutaraldehyde or other reducing agent.

It is usually desirable to incorporate the non-biodegradable particles, such as collagen, with the fat receptors thereon into a complex with an emulsifying agent. The food fats, when released from the food and many of the non-biodegradable particles, such as for example, collagen, are generally insoluble in water which would otherwise be the main carrier for any such particles in the gastrointestinal tract. Thus, the non-biodegradable particles with receptors thereon are usually bound with an emulsifying agent such as acacia.

In one of the preferred embodiments of the present invention, bile is the preferred fat receptor. Bile is also one of the components generated by the body to accummulate the fat within the body and thus, serves as an excellent fat receptor on the non-biodegradable particles to accummulate the fat and cause the passage of the fat from the body through the body excretia.

The particles which may be employed in the present invention are non-biodegradable, and may adopt the form of ground collagen, as aforesaid. One of the preferred particles which has been found to be highly effective in the present invention are the non-biodegradable plastic microspheres. Further, it has also been found to be effective to create an emulsion of the particles with another substance such as a gum, e.g. guar gum.

The bile or other fat receptor is attached to the cross-linked collagen particles or the microsphere or other non-biodegradable fibers. The fat actually becomes attached to the fat receptor and not to the fiber as such. Moreover, the , emulsifier, such as acacia gum, operates to actually encapsulate the fat and bile onto the non-biodegradable particle. Moreover, the emulsifier operates to accumulate water into the combination.

The present invention also relates to a composition for collecting and binding dietary fat which is released from a food product in an animal gastrointestinal tract. The composition comprises the non-biodegradable particles having a size within the range of at least about 2 microns and which are sufficiently large such that they will not pass through the surface mucosa of the gastrointestinal tract. The particles comprise a fat receptor on the surface thereof, as aforesaid, to adhere food fat thereto and which permits the attached food fat to pass through the gastrointestinal tract and out of the body through the body excretia.

The method and compositions of the present invention have also been found to be effective in improving the ratio of the high density lipoprotein cholesterol to the low density lipoprotein cholesterol. It has been found that the fat receptor - non-biodegradable particles will actually block the absorption of free fatty acid biocomplex. Hence, there is less fat available to produce the low density lipoprotein cholesterol which is associated with higher risk coronary problems. As a result, there is a higher ratio of high density lipoprotein cholesterol which is circulated in the body bloodstream.

It has also been found in connection with the present invention that by binding the fat with an emulsifying agent to the non-biodegradable particles, there is significantly less water absorption from the digested food product passing through the large intestinal tract. As a result, the method and the composition of the present invention inherently provide control over the water absorption by the body and hence constipation. Thus, the method and the composition of the present invention are also effective in reducing constipation as well as in reducing fat absorption by the body.

The method of the present invention has many other advantages and has other purposes which may be made more clearly apparent from a consideration of the forms in which both the method and the composition may be embodied. These forms are set forth in the following detailed description. However, it is to be understood that the detailed description is only for purposes of illustrating the general principles of the present invention and that it is to be understood that such detailed description is not to be taken in a limiting sense.

BRIEF DESCRIPTION OF THE DRAWING

Figure 1:
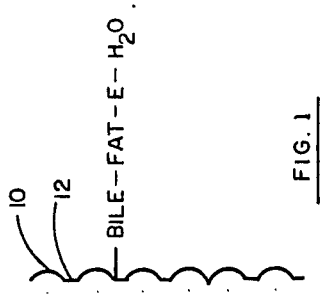
Figure 2:
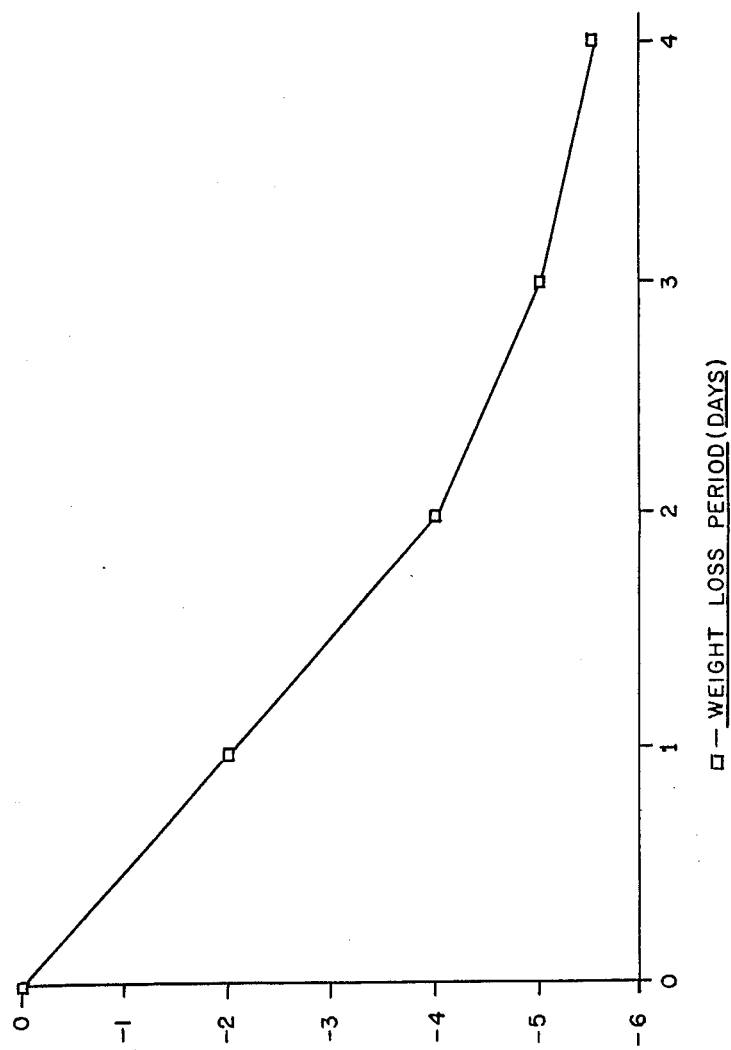

Having thus described the invention in general terms, reference will now be made to the accompanying drawing in which:

FIG. 1 is a schematic illustration showing the relationship of the various components forming part of the composition and its operation in accordance with the present invention; and FIG. 2 is a graphical illustration showing the effect of weight loss as a function of the time period of using the composition and method of the present invention.

DETAILED DESCRIPTION OF THE PREFERRED EMBODIMENTS

The present invention relies upon the use of fat receptors on non-biodegradable particles to absorb food fat in the gastrointestinal tract and thereby preclude absorption of the fat by the body. In accordance with this method and composition, the food fat will pass completely through the gastrointestinal tract and out of the body through the body excretia.

It is well established that the production of bile in the human body is used to absorb dietary fats. Inasmuch as the food fats would not be soluble in any polar liquid, such as water, the body emulsifies the fats which are released from food particles in the stomach and creates a liquid emulsion. This liquid bile emulsion passes as droplets into the biliary vein and then into the liver. The liver generates lipoproteins from the fats which are then introduced into the bloodstream. As a result, the fats are, in effect, absorbed by the body.

It is believed that cholesterol is possibly the major and ever more possibly the sole precursor of bile acids which are generated. During normal digestion, bile acids are secreted via the bile from the liver and gall bladder into the intestines. Bile acids emulsify the fat and lipid materials present in food. In this way, absorption is facilitated. A major portion of the bile acid secreted is re-absorbed from the intestines and returned via the portal circulation to the liver. In this way, the enterohepatic cycle is completed.

It has been discovered in connection with the present invention that if a mechanism were provided to interfere with the absorption of the fat by the body, usually in the duodenum, then the fat would generally pass through the gastrointestinal tract and out of the body with the body excretia. One of the important aspects is that the particles to which the fat become attached must be sufficiently large so that they do not pass through the surface mucosa of the intestines and moreover, must be non-biodegradable.

It has been found in accordance with the present invention that the administration of the non-biodegradable particles with the fat receptors thereon is effective to reduce generation of the low density lipoprotein cholesterol (often referred to as LDL cholesterol) and to promote a greater generation of the high density lipoprotein cholesterol (often referred to as HDL cholesterol). The Spheres effectively block the absorption of the free fatty acid bile complex by the body. Hence, there is less fat available to the liver for production of the LDL cholesterol. As a result, the body will mobilize the tissue of the body to generate the HDL cholesterol. Consequently, it has been found in accordance with the present invention that the method and compositions of the present invention not only reduce the amount of body fat for purposes of weight control, but they also reduce the amount of low density cholesterol in the body blood stream.

The particles which are used may be initially non-biodegradable, such as the microspheres, as aforesaid. Otherwise, the particles may be rendered non-biodegradable, as for example, by cross-linking. In each case, it is necessary for the fat receptor to be attached to the surface of the particle for enabling adherence of the food fat thereto. A schematic illustration of the arrangement of the fat receptor, such as bile, on the particles with the fat adhered thereto is more fully illustrated in FIG. 1. In this case, 10 designates certain particles, such as collagen particles and which are cross-linked by cross-linking bonds 12 as a result of a cross-linking agent. Fat receptors such as the bile are attached to the chain of the various collagen particles. Moreover, the fat literally becomes attached to the bile or other fat receptor, in the manner as illustrated.

It is also important to employ an emulsifier in accordance with the present invention. The emulsifier can be administered individually along with the biodegradable particles, or the emulsifier can be mixed with the biodegradable particles and administered as a mixture thereof. The emulsifier is effective to generally encapsulate the fat and the bile on the non-biodegradable particles. Moreover, and as indicated above, the emulsifier is effective to create an environment where the fat is maintained in a liquid phase. This will reduce the possibility of constipation, gas generation and other complications which could arise in the lower gastrointestinal tract.

One of the most preferred forms of particles which have been found are fibrous particles such as, collagen. Even more so, tanned collagen is preferred. The tanned collagen can be cut into sheets and ground into small particles. When provided with a suitable fat receptor, the ground particles are capable of absorbing dietary fats of three to four times their own weight.

Other non-biodegradable substances which may be used include cross-linked albumen as well as numerous other animal and vegetable proteins which are not digestable, such as cellulose.

One of the more preferred forms of particles which has been found to be effective in the present invention are non-biodegradable microspheres. The microspheres which may be used in accordance with the present invention usually are comprised of long chain compounds susceptible to cross linking to a solid in which amide or carboxyl groups are exposed, or are capable of being exposed, by suitable treatment. This includes, but is not limited to latex materials such as polystyrene and styrene divinylbenzene, agarose, polyalkylcyanoacrylate, albumin, cross-linked albumin, sucrose, starch, cellulose and dextran.

The microspheres can be stored for a substantial period of time and therefore are highly effective. Usually, latex microspheres are stored with a colloidal silica coating and with the coated spheres forming a 10 percent solid suspension in water. Generally, before the application of the fat receptors, the microspheres may be cleaned by vacuum filtering and drying.

As indicated above, it is necessary to apply a fat receptor to the surfaces of the particles. One of the most preferred fat receptors is that of bile, inasmuch as the bile is found to be highly effective in attaching the fat in the body itself. Another receptor which can be employed is the cholestyramine powder. Generally, any of the bile salts may be used as fat receptors.

Another highly effective fat receptor which may be employed in accordance with the present invention is colestipol hydrochloride which is offered under the name Colestid. The colestipol hydrochloride is generally present in the form of a high molecular weight basic anion-exchange copolymer comprised of diethylenetriamine and 1-chloro-2, 3-epoxypropane. Another fat receptor which may be used in accordance with the present invention is gemfibrozil often offered under the commercial name "Lopid", usually adapted for oral administration. The gemfibrozil is generally comprised of 5-(2,5-dimethylphenoxy)-2,2dimethylphenoxy acid having an empirical formula of $C_{15}H_{22}O_3$. Still a further suitable fat receptor is niacin often offered under the commercial name "Nicolar" and which is primarily nicotinic acid. The niacin functions in the body as a component of hydrogen transporting coenzymes nicotinamide adenine dinucleotide (NAD) as well as nicotinamide adenine dinucleotide phosphate.

Several emulsifiers may be used to create the emulsified solution of the fat attached to the fat receptor particles. The emulsifier generally creates an intimate mixture between the two components which would otherwise be immiscible. The emulsifier thereby provides a stable emulsion. One of the preferred emulsifying agents is acacia gum which is the dried gummy extract from the stems and branches of the acacia plant. Generally, the acacia gum consists primarily of the calcium salt of arabic acid which will yield galactose and arabinosic acid when hydrolized. Other emulsifiers which may be used include guar gum which is often sold under the trade designation "Guarem". Other emulsifying agents which can be used include sodium alginate, sodium lauryl sulfate, gum arabic, etc. In essence, any emulsifying agent which is not incompatable with the body and which is capable of emulsifying the fat and non-biodegradable particles may be employed.

It is oftentimes desirable to tan the non-biodegradable particles which are used. In effect, the non-biodegradable particles are cross-linked to bi-functional groups such as glutaraldehyde. However, the tanning process is not required.

The non-biodegradable particles must be of a proper size, usually no less than about 2 microns and preferably, the particles are no less than about 5 microns. In this way, they will not pass through the surface mucosa of the intestinal tract. There is generally no upper limit on the size of the particles, since it is only necessary that the particles be sufficiently large to preclude passing through the surface mucosa of the gastrointestinal tract. However, as a matter of practicality, the particles usually do not exceed about 50 microns, although that clearly is not a maximum upper limit.

Usually, the fat receptors are bound to the non-biodegradable particles in water baths. The non-biodegradable particles, such as collagen, are usually dispersed in water using a rather vigorous mixing. The fat receptor is also dissolved in water, generally in an acid pH as for example, about 2 to 4, and preferably a pH of 3 and the two mixtures are then blended. An emulsifier, is then added to the solution to cause an emulsification thereof. Thereafter, the liquid can be air dried to provide a solid composition.

The present invention thereby provides a unique and novel composition comprised at least of a non-biodegradable particle, or particle which has been rendered non-biodegradable in a complex with a fat receptor such as bile. Thus, a novel composition in the form of collagen and bile has been provided. In addition, the present invention provides a novel formulation of the complex of particle and fat receptor along with an emulsifying agent therefore such as the gum acacia. Further, the present invention provides a unique and novel method of using these compositions to not only reduce weight, but to reduce the adverse low density serum cholesterol levels and also to improve the passage of stool from the body.

EXAMPLES

The invention is further illustrated by but not limited to the following examples:

Example 1

This example describes the preparation of a composition used to collect and bind dietary fat.

Bovine achilles tendon collagen was used to form the non-biodegradable particles or carrier, although any other source of collagen could be employed. The achilles tendon collagen was introduced into a chilled Waring blender in an amount of about 500 mgs. Thereafter, 100 milliliters of dispersed water was introduced into the blender such that the collagen was fully dispersed in the blender. The pH of the water was adjusted to an acidic pH of about 3 by pouring lactic acid into the water. Blending of the collagen in the water carrier occurred by periodically operating the blender in 10 second bursts.

A second solution of porcine bile extract was dissolved in three milliliters of distilled water. Approximately 300 mgs. of the porcine bile was used. The pH of the water was also controlled to about an acid level of pH 3. Thereafter, the two solutions were blended.

A 25 percent solution of glutaraldehyde was used as the cross-linking agent and was added to the mixed solution to provide a five percent concentration. Vigorous mixing occurred thereafter. The resultant composition constituted a fibrous preparation of cross-linked collagen entrapped with bile extract. The composition was then spread upon a paraffin film and air dried. It was determined that the recovery was approximately 70 percent to about 90 percent of the initial weight of input materials.

EXAMPLE 2

This Example 2 describes the binding of dietary fat to the fiber-bile composition prepared in accordance with Example 1.

The binding of food fats to the fiber-bile composition was tested by measuring the activity of bile acid. Any unbound bile, that is bile which did not have fat bound thereto, would inherently display a bile acid activity. The activity of bile acid was measured by using a coupled enzyme reaction with three-alpha-hydroxy steroid dehydrogenase with the coenzyme, nicotinamide adenine dehydrogenase (NAD).

A plot of a standard curve of the reaction is linear in accordance with Beer's law. When either the free fatty acid released from the food product or cholesterol is bound to the bile acid, the bile acid activity is reduced or eliminated. Accordingly, the binding of the food fat can be measured by following the inhibition of bile acid activity.

In order to test the binding of food fats to the fiber-bile complex of Example 1 the bile acid activity was tested both with and without sodium palmitate. The fibrous-bile complex composition was incubated with a solution of sodium palmitate. Moreover, the sodium palmitate was prepared according to the procedure recommended by Van Harken et al in the Journal of Biological Chemistry, 244(9):2278, 1969. The suspension of the fibrous-biocomplex in the sodium palmitate was found to be stable in a glycerine-hydrazine assay solution.

10 mgs. of the collagen preparation was incubated at 37 degrees for about one hour with 0.5 milliliters of the sodium palmitate. At the completion of the incubation period, the eluates were removed and bile activity was tested. A control of bile acid activity without the sodium palmitate was also used in connection with this evaluation. The bile acid activity without the sodium palmitate was 454 units and the bile acid activity with the sodium palmitate was 205 units. This provided a 54 percent reduction which was proportional to the percent of fat binding to the non-biodegradable particles.

Example 3

A test for the binding of fat was conducted similar to that of Example 2. However, in this test, sodium oleate was employed in place of the sodium palmitate, inasmuch as sodium oleate was another free fatty acid which had properties similar to that of the sodium palmitate.

The same test of Example 2 was conducted and in the absence of sodium oleate, the activity in a 10 mg. solution of the collagen-bile was 66 od units. However, the bile acid activity in the presence of the sodium oleate was only 33 units which resulted in a 50 percent reduction.

Example 4

The following example describes the use of fat binding pills which were prepared for use with human beings.

In accordance with this Example 4, the pills which were prepared incorporated the collagen-bile complex with the emulsifying agent prepared in accordance with Example 1. However, in this case, acacia was used as the insoluble carbohydrate complex emulsifying agent. The emulsifying agent and the collagen-bile complex were introduced into a container in equal amounts and then made in the form of gelatine capsules. The initial capsules contained 500 mgs. of each of the emulsifying agent and the collagen-bile complex agent.

Example 5

A normal adult male was placed on a mild calorie restriction diet of 1800 calories with a normal calorie intake of about 2200 calories per day. A one gram capsule in accordance with Example 4 was taken with each meal.

The weight of the man was taken each morning at the same time and a complete blood profile was taken before and at the end of a one week period. The regimen described herein resulted in a 7 pound weight loss. FIG. 2 illustrates the weight loss period in days and specifically identifies the effect of fat receptive particles on body weight. The total serum cholesterol did not materially change. The HDL cholesterol did increase from about 27 to about 85 with a proportional fall in the LDL cholesterol. The stool of this man showed a visible increase in fat content by virtue of its flotation on water.

Example 6

A normal adult female was given a diet which was designed to cause a weight change. In this case, approximately 3,000 calories per day were given to the adult female, as opposed to a normal consumption of about 2300 calories. This regimen resulted in a 1.5 pound weight decrease over about a one week period. There was no change in cholesterol pattern. However, there was visible fat in the stool with a substantial increase in stool bulk. Further, there was no adverse side effects in this Example 6 or in Example 5.

Example 7

A normal adult female was also given a diet designed to cause a weight reduction. The diet provided approximately 1400 calories per day and which was less than the normal consumption of about 2300 calories per day. This program continued for about 3 weeks resulting in a 16 pound reduction in weight.

The HDL level of the same female increased from 23 units at the beginning of the three week period to 38 units at the end of the three week period. Further, the low density lipoprotein cholesterol was reduced from 155 units at the beginning of the three wee period to 140 units at the end of the three week period.

Thus, there has been described a unique and novel process and composition for reducing weight and reducing HDL cholesterol by reducing absorption of food by an animal body. Thus, the present invention fulfills all of the objects and advantages which have been sought. It should be understood that many changes, modifications, variations and other uses and applications will be apparent to those skilled in the art after considering this specification. Therefore, any and all such changes, modifications, variations and other uses and applications which do not depart from the spirit and scope of the invention are deemed to be covered by the invention.

Having thus described the invention, what I desire to claim and secure by letters patent is:

1. A method of collecting and binding and expelling from a body, dietary fat released from food products in an animal gastrointestinal tract, said method comprising:
   (a) introducing non-biodegradable collagen particles into an animal gastrontestinal tract and which are of a size such that they will not pass through the surface mucosa of the gastrointestinal tract, said particles havinq fat receptors on a surface thereof to attract and bind food fats thereto,
   (b) allowing food fats releasd from food in the gastrointestinal tract to become attached to the fat receptors on the particles, and
   (c) permitting the fat laden non-biodegradable collagen particles to pass through the gastrointestinal tract and out of the body with body excreta.

2. A composition useful in collecting and binding fat thereto which is released from food products in an animal gastrointestinal tract, said composition comprising non-biodegradable collagen particles having a size of at least two microns and a fat receptor capable of adhering food fat thereto on the surface of such particles, such that the particles are sufficiently large that they will not pass through the surface mucosa of the gastrointestinal tract but will attract the fat released from the animal food and permit the fat attached particles to pass through the gastrointestinal tract and out of the body through the animal excreta.

* * * * *